United States Patent [19]

Thompson

[11] Patent Number: 5,298,197

[45] Date of Patent: Mar. 29, 1994

[54] CHEMILUMINESCENT MICROEMULSIONS

[75] Inventor: Richard Thompson, Baltimore, Md.

[73] Assignee: The United States of America as represented by the Secretary of the Navy, Washington, D.C.

[21] Appl. No.: 253,635

[22] Filed: Oct. 6, 1988

[51] Int. Cl.$^5$ ................................................. C09K 3/00
[52] U.S. Cl. ..................... 252/700; 252/186.28; 252/186.29; 252/301.16
[58] Field of Search ............. 252/700, 186.28, 186.29, 252/301.16

[56] References Cited

U.S. PATENT DOCUMENTS

| | | | |
|---|---|---|---|
| 3,969,263 | 7/1976 | Richter et al. | 252/700 |
| 4,053,430 | 10/1977 | Mohan | 252/700 |
| 4,146,499 | 3/1979 | Rosano | 252/186.25 |
| 4,405,513 | 9/1983 | Kamhi | 252/700 |
| 4,450,305 | 5/1984 | Kamhi | 252/700 |
| 4,462,931 | 7/1984 | Cohen et al. | 252/700 |
| 4,547,317 | 10/1985 | Kamhi | 252/700 |
| 4,647,532 | 3/1987 | Watanabe et al. | 435/28 |
| 4,859,369 | 8/1989 | Baretz et al. | 252/700 |

*Primary Examiner*—Philip Tucker
*Attorney, Agent, or Firm*—Thomas E. McDonnell; A. David Spevack; Barry A. Edelberg

[57] ABSTRACT

The invention is directed to a light producing microemulsion formed in the presence of a surfactant/cosurfactant pair from an oil phase medium having at least an oxalate derivative and a fluorescer compound dissolved in it and an aqueous phase medium containing at least an oxidant dissolved in it. The light produced in such a microemulsion can be used to analyze aqueous oxidant-containing samples by comparing the amount of light produced by a microemulsion formed from a known quantity of an oxidant to a similar sample containing an unknown quantity of an oxidant. The comparison can be made by any well known photosensitive means and can be computerized.

10 Claims, No Drawings

CHEMILUMINESCENT MICROEMULSIONS

BACKGROUND OF THE INVENTION

1. Field of the Invention

The present invention relates to a novel chemiluminescent microemulsion which can be used as an analytic tool for the detection of oxidants in aqueous samples. In addition, the present invention relates to an analytic technique and analytic arrangement which uses peroxyoxalate chemiluminescence in a microemulsion to determine the approximate oxidant concentration of an aqueous sample.

2. Description of the Prior Art

The detection of the approximate concentration of pollutants or contaminants, particularly those which generate an oxidizing agent such as hydrogen peroxide, by chemiluminescent analysis is well known. The detection of peroxide has been reported using luminol chemiluminescent techniques by G. L. Kok, et al., *Envir. Sci. Technol.*, 12, pp.1072–1076 (1978); DeChatelet, L. R., et al., *J. Immunol*, 129, pp.1589–1593 (1982); B. Descamps-Latscha, et al., *Ann. Immunol.*, 133, pp.349–364 (1982); and P. De Sole, et al., Adv. *Exp. Med. Biol.*, 141, pp.591–601 (1982). Also, lucigenin chemiluminescence analysis in micellar systems has been described by W. L. Hinze et al. *Anal. Chem.*, 56, p.2180 (1984).

However, the reported methods have several drawbacks. They are not very sensitive or efficient for the detection of oxidants, particularly hydrogen peroxide. Another drawback is that these prior art reactions require operating at a very high pH which necessitates adding large quantities of a strong base. This increases the risks of introducing contaminants and interferents such as metal ions.

The overall process of the peroxyoxalate chemiluminescence system, first described by Edward A. Chandross, *Tetrahedron Letters*, No. 12, p.761, (1963) and disclosed in U.S. Pat. No. 4,053,430, consists essentially of the reaction of an oxalic acid ester with $H_2O_2$ in the presence of a fluorescer compound to generate chemiluminescence. The reaction sequence can be described by the following three steps: (1) An oxalate derivative is oxidized by an oxidizing agent such as $H_2O_2$ to form the putative dioxetanedione intermediate, (2) this intermediate breaks down and transfers its energy to a fluorescer also present in the system, (3) the fluorescer then emits a photon. This system is very efficient. Despite the system's broad use for illumination, the prior art methods have not been used in chemical analysis because of the insolubility and lability of the chemiluminescent reagents in aqueous medium.

G. Scott, W. R. Seitz and J. Ambrose, *Anal. Chem. Acta*, 115, p.221 (1980) report grave difficulties with attempts to find compatible solvents for quantifying aqueous $H_2O_2$ in a peroxyoxalate chemiluminescent flow injection system. A. G. Mohan et al., "Aqueous Peroxyoxalate Chemiluminescence," AD121,396, Defense Technical Information Center, Cameron Station: Alexandria, Va. 22304–6145, p.16, (1982), describe the peroxyoxalate chemiluminescent reaction in a cyclohexane in water emulsion. They reported no significant improvements in results. In additional work, they reported that better results were obtained when a detergent was included.

In U.S. Pat. No. 4,647,532, Watanabe et al. describe a method for the detection of hydrogen peroxide using a chemiluminescent method. This method involves a complex, multistep reaction of a hydrogen peroxide component in the presence of an oxidizing catalyst to convert a nonfluorescer substance to a fluorescer substance and then reacting the fluorescer substance with an oxalic acid diester and hydrogen peroxide to produce light.

None of the above methods is efficient in producing chemiluminescence or for adapting chemiluminescence to analytic techniques. The most efficient fluorescent compounds useful in peroxyoxalate chemiluminescence, including rubrene, perylene, and bis-(phenylethynyl)anthracene, are all insoluble in water. The most efficient oxalate derivatives, including amides and esters, have strong electron withdrawing groups that favor hydrolysis in aqueous solution. This insolubility and lability of the oxalate derivatives and fluorescers in aqueous media or other protic solvents is a limiting factor for the successful use of peroxyoxalate chemiluminescence as a light source or in analytic chemistry.

SUMMARY OF THE INVENTION

Accordingly, an object of this invention is to provide a suitable environment for the reaction of the chemiluminescent reagents in an aqueous medium.

Another object of this invention is to promote the reaction between the hydrophilic hydrogen peroxide component and the hydrophobic oxalate derivative in an aqueous medium.

An additional object of this invention is to increase the efficiency and rate of the reaction by maximizing the amounts of the components present and facilitate their mixing by maximizing the interfacial surface area between components.

Yet an additional object of this invention is to isolate the fluorescer compound from quenchers which may be present in an aqueous medium.

A further object of this invention is to maintain the oxalate derivative and fluorescer compound together at a high concentration to maximize efficient energy transfer from the former to the latter.

Yet a further object of this invention is to provide a macroscopically homogenous, transparent microemulsion that is thermodynamically stable so as to maximize light release and detectability.

These and other objects of the invention are accomplished by forming a light producing microemulsion in the presence of a surfactant/cosurfactant pair from an oil phase medium having at least an oxalate derivative and a fluorescer compound dissolved in it and an aqueous phase medium containing at least an oxidant dissolved in it. The light produced in such a microemulsion can be used to analyze aqueous oxidant-containing samples by comparing the amount of light produced by a microemulsion formed from a known quantity of an oxidant to a similar sample containing an unknown quantity of an oxidant. The comparison can be made by any well known photosensitive means and can be computerized.

DETAILED DESCRIPTION OF THE INVENTION

The present invention permits peroxyoxalate chemiluminescence to occur in aqueous media with greater sensitivity and efficiency. The microemulsion permits the utilization of peroxyoxalate chemiluminescence for the semi-quantitative determination of oxidants in aqueous media. The microemulsions of this invention may be formed as oil-in-water or water-in-oil microemulsions. By the compositions and methods of this invention chemiluminescence can be observed and detected when the microemulsion mixture is exposed to a sample containing an oxidant, preferably $H_2O_2$, which is produced by natural processes in water sources or is added to the water system. The methods and compositions of this invention permit the detection of $H_2O_2$ concentrations in quantities as small as $10^{-9}M$ and has been found to be particularly effective as an indicator of aquatic pollutants at sea.

Microemulsions (also known as Winsor IV phases or swollen micellar solutions) have been defined as thermodynamically stable, isotropic solutions of surfactant, oil and water. (Danielson, I. and Lindman, B., *Colloids Surf,* 3, 393 (1981)). Because of their unique properties, microemulsions are particularly useful for carrying out reactions employing immiscible reagents. More importantly, microemulsions may contain up to 10% oil in water or vice versa and yet be completely stable and optically clear.

Optical clarity is of special interest in this invention because it is desirable that the reaction mixture be transparent to the wave length of light produced by the reaction and not to turbid so as to maximize light release and detectability. This property is refered to herein as the medium being optically transparent. It is most preferred that the oil phase and all compounds dissolved in the oil phase of this invention be substantially clear and transparent. The aqueous phase of this invention should also be substantially clear although some turbidity is expected if test samples are taken from bodies of water in an exposed environment such as water tanks, reservoirs, lakes, rivers, and oceans.

The compositions of this invention are those microemulsions which consist of substantially small, about 1000Å or less, droplets of one phase suspended indefinitely in the other phase. Oil-in-water microemulsions are the most preferred embodiment of this invention.

Because the reaction of the aqueous miscible and immiscible reagents takes place at the organic solvent/aqueous interface, the microemulsion facilitates contact of the reagents by maximizing the interfacial surface area between the aqueous and nonpolar phases. Moreover, because the microemulsion is thermodynamically stable—i.e., it does not separate into oil and water phases—it makes prolonged, vigorous or ultrasonic mixing unnecessary. A great variety of microemulsions have been formulated, however, it is well known that only particular components combined in specified proportions will form stable, transparent microemulsions of tiny droplets.

The formation of a microemulsion of this invention requires the presence of about 10 to 30% by weight of an ionic or nonionic surfactant/cosurfactant pair. The term surfactant/cosurfactant pair as used herein is defined as surface active agents that lower the surface tension of a liquid or the interfacial tension between two liquids. Typical examples of suitable surfactant/cosurfactant pairs which may be employed include sodium dodecyl sulfate/1-butanol; Triton X-100/1-hexanol; cetyltrimethylammonium bromide/1-butanol; Brij 96/1-butanol; sodium oleate/1-butanol. Triton is a trademark product of Rohm and Hass and Brij is a trademark product of ICI America. Of course, any surfactant/cosurfactant pair can be used which permits the formation of an optically transparent microemulsion.

The oil phase material may be any of the water immiscible, nonpolar organic materials which are optically clear and will form optically clear microemulsions. The materials may be aliphatic or aromatic solvents. Also, the oil phase material should be non-reactive with the reagents and compounds likely to be encountered in the microemulsion, and the materials must be solvents for the fluorescer materials and oxalate derivatives. Preferred oil phase materials include toluene and tetradecane.

Any aqueous media from distilled water to sea water can function as the aqueous phase in microemulsions of this invention. Generally, low electrolyte concentrations are preferred with nonionic microemulsions (for example, those containing Triton X-100, Tween or Brij-96), whereas higher ionic strengths are preferred with ionic microemulsions (for example, those containing sodium dodecyl sulfate, oleic acid, or cetyltrimethylammonium). In the preferred embodiment the aqueous phase contains about 0.4 M NaCl in addition to the oxidant material.

According to the present invention, the reactants of the chemiluminescent system are kept separate from the microemulsion medium until chemiluminescence is desired. The order of admixing the reactants in the microemulsion is not critical. The reactants may be admixed in a single step or in a series of steps. Preferably, the fluorescer and oxalate derivative are dissolved in the oil phase, to which are added successively the surfactant/cosurfactant mixture, and an aqueous sample.

The aqueous sample contains at least the oxidant. The aqueous sample can also contain salts, color enhancers or catalysts such as sodium salicylate. Together, in the proper proportions, these materials form a clear, transparent homogenous phase. When the system is just used to generate chemiluminescent light, hydrogen peroxide is used as the oxidant.

The molar concentrations (moles per liter of solution) of the components of the chemiluminescent system, described herein, may vary considerably without changing the ability to use the system for light generation and hence, semi-quantitative analysis. It is only necessary that the components be present in sufficient concentrations to obtain chemiluminescence.

The molar concentration of the oxalate derivative is in the range of 1 to 20 mM, preferably about 5 mM. The molar concentrations of the fluorescer compound used is from $10^{-6}M$ to 1 mM, preferably 0.2 mM.

The detectable molar concentration of the unknown oxidant or the standard hydrogen peroxide is from about $10^{-9}M$ to 1 M. With improved detection methods, it is expected that even lower concentrations of oxidant materials should be detectable. The molar concentration of the sodium salicylate catalyst used is from 1 mM to 30 mM, preferably 10 mM.

The color of the chemiluminescent emission corresponds to the known fluorescence of suitable fluorescers. Illustrative examples of the fluorescent compounds employed herein include the following:

1-chloro-9,10-bis (phenylethynyl) anthracene; perylene; 2-chloro-9,10-bis (p-methylphenyl) anthracene, 6,13-bis (p-methylphenylethynyl) naphthacene; many fluorescent aromatic amines, including 3-aminofluoranthene, 1-anilinonaphthalene-8-sulfonate, 2-toluidinylnaphthalene-6-sulfonate, aminopyrene, Dansyl amino acids, fluorescein and rhodamine derivatives; polynuclear aromatic hydrocarbons and their derivatives, including rubrene sulfonate and pyrene; and coumarins.

Many other fluorescers are known to produce light in peroxyoxalate chemiluminescent reactions and any of these can be used in this invention. The efficiency of each fluorescer is related to its oxidation potential. The selection of a particular fluorescer will be within ordinary skill of people working in the field.

Any oxalic acid bis-amide or bis-ester with electron withdrawing substituents on the amine or alcohol moieties will serve in the reaction. These are referred to generically herein as oxalate derivatives. Methods of preparation for many of these oxalate derivatives, particularly acid esters, are well described in the literature. The American Cyanamid Company has described dozens of such compounds. Several of the esters are available from commercial sources. Typical oxalate derivatives used in this invention include the following: bis (2-(carboisopentyloxy)-3,5,6-trichlorophenyl) oxalate, bis [N-2-(N'-(N'- methyl) morpholinium) ethyl-N-trifluoromethylsulfonyl]oxamide bis-trifluoromethanesulfonate, bis (2,4,6-trichlorophenyl) oxalate, and bis (2,4-dinitrophenyl) oxalate.

Additionally, it has been found that a significant proportion of the oxalate derivative (0.2%) remains intact in the microemulsion after 16 hours. Although the oxalate derivative is not stable indefinitely in the microemulsion system, a half-life of about 1 hour is generally displayed.

The initial intensity approximately doubles as the temperature is raised from 6° to 52° C. It should be noted, however, that the decay rate also increases six-fold, which suggests that raising the temperature increases the reaction rate without really changing the total quantum yield.

The intensity of the light generated by the reaction is proportional to the amount of oxidant present if all other factors, such as the amount of flourescer, are the same. The approximate quantity of an uknown oxidant can be estimated by comparing the light output of a known sample or samples to the light output of an unknown sample.

In general, the comparison is done by providing a substantially optically transparent oil phase material for a microemulsion. Dissolving at least a fluorescer compound and an oxalate derivative in the oil phase material. Taking equal aliquots of the oil phase material to form at least two oil phase material portions. It is good practice to have several known standardizing samples. When that practice is followed, an aliquot is made for each sample. The microemulsion requires a surfactant/cosurfactant pair. To maintain equal conditions, an aliquot for each sample of a surfactant/cosurfactant pair is also taken. At least one aqueous sample containing a known quantity of an oxidant material is prepared. To improve the quantitative accuracy, it is preferred to have several known samples of different concentrations. An aqueous sample containing an unknown quantity of an oxidant is also prepared. The volume of the known and unknown samples should be the same. The known containing aqueous sample or samples, an aliquot of said surfactant/cosurfactant pair, and an aliquot of said oil phase material are mixed to form a known containing microemulsion sample or samples. The amount of light produced in the known containing microemulsion sample is read with a photo-sensitive reading means such as a Spex Fluorolog 2 (or other) fluorimeter operated without a lamp, a photodiode, charge-coupled device, photo film, or a luminometer. Similarly, the unknown-containing aqueous sample, an aliquot of said surfactant/cosurfactant pair, and an aliquot of said oil phase material is combined to form an unknown containing microemulsion sample and its light output is read in the same device used for the known samples. Lastly, the readings of the known and unknown containing samples are compared and the approximate quantity of oxidant in the unknown sample determined. Of course, this can be done automatically by computer.

Having described the invention the following examples are given to illustrate specific applications of the invention. These specific examples are not intended to limit the scope of the invention described in this application.

EXAMPLE 1

The oxalate ester (bis (2-(carbopentyloxy)-3,5,6-trichlorophenyl) oxalate (1.3 mg/ml total volume) and the fluorescer compound (1-chloro-9,10-bis (phenylethynyl) anthracene (1 mg/ml) are dissolved in toluene. The surfactant/cosurfactant pair is sodium dodecyl sulfate/1-butanol (3:5, w/w). Sodium salicylate catalyst (0.2 mg/ml) is added to the aqueous sample. The sample is made saline by adding salt to a concentration of 0.4M NaCl. The standard or known is 100 ul of 30% $H_2O_2$.

Aliquots of the oil phase material and surfactant/cosurfactant pair are taken and the three parts are combined. When the oil phase material aliquot, surfactant/cosurfactant pair aliquot, and aqueous samples are each combined an oil/water microemulsion (0.09: 0.43: 0.48, v/v respectively) is formed. Readings are taken using a Spex Fluorolog 2 fluorimeter operated without a lamp. The readings are compared and the quantity of unknown oxidant estimated. The quantum yield of the known is approximately 2%.

EXAMPLE 2

Following the procedure of Example 1 Brij-96/1-butanol (2:1, w/w) is utilized as the surfactant/cosurfactant pair in an oil:water:c/s configuration (0:10: 0.40: 0.5, v/v) and water:oil:c/s configuration (0.63: 0.06: 0.31, v/v).

EXAMPLE 3

Following the procedure of Example 1 Triton X-100/1-hexanol (4:1, w/w) is utilized as the surfactant/cosurfactant pair in an oil:water:c/s configuration (0.49: 0.02: 0.49 v/v) and water:oil:c/s configuration (0.06: 0.47: 0.47 v/v).

EXAMPLE 4

Following the procedure of Example 1, cetyttrimethylammonium bromide/1-butanol (1:1, w/w) is utilized as the surfactant/cosurfactant pair in an oil:-water:c/s configuration (0.06: 033: 0.61, v/v). The quantum yield of this reaction is very low and can be attributed to the presence of the bromide ion, a well-known fluorescence quencher.

EXAMPLE 5

Following the procedure of Example 1, perylene is utilized as the fluorescent compound. The same procedure is repeated using 2-chloro-9,10-bis (p-methoxyphenyl)anthracene, 6,13-bis (p-methylphenyl) ethynyl) naphthacene, and rubrene as fluorescers, respectively. The intensity of the reaction generally increases with fluorescer concentration but no increase in intensity over 1 mg/ml is observed at 10 mg/ml concentration.

EXAMPLE 6

Following the procedure of Example 1, bis [N-2-(N'-(N'-methyl) morpholinium) ethyl-N-trifluoromethylsulfonyl] oxamide bis-trifluoromethanesulfonate is utilized as the oxalate derivative. The surfactant/cosurfactant pair, fluorescer and microemulsion configuration are the same as in Example 1.

EXAMPLE 7

Following the procedure of Example 3, bis (2,4,6-trichlorophenyl) oxalate is utilized as the oxalate derivative. Note that this oxalate derivative was not solubilized well in the sodium dodecyl sulfate/1-butanol system. The other oxalates also seemed to be less effective than the commercially used bis (2-carbopentyloxy)-3,5,6-trichlorophenyl)oxalate.

Obviously, many modifications and variations of the present invention are possible in light of the above teachings. It is therefore to be understood that within the scope of the appended claims, the invention may be practiced otherwise than as specifically described.

What is claimed is:

1. A composition for producing light by peroxyoxalate chemiluminescence comprising a microemulsion which is optically transparent to light produced by peroxyoxalate chemiluminescence, said microemulsion comprising:
   an oil phase containing at least a fluorescer compound and an oxalate derivative,
   an aqueous phase containing at least an oxidizing agent, and a surfactant/cosurfactant pair present in an amount sufficient to form said microemulsion.

2. A composition according to claim 1, wherein the oxidizing agent is hydrogen peroxide.

3. A composition according to claim 2, wherein the oxalate derivative is an oxalic acid ester selected from the group consisting of bis(2-(carboisopentyloxy) 3,5,6-trichlorophenyl) oxalate, bis [N-2-(N'-(N'-methyl) morpholinium) ethyl-N-trifluoromethylsulfonyl] oxamide bis-trifluoromethanesulfonate, bis (2,4,6-trichlorophenyl) oxalate, bis (2,4-dinitrophenyl) oxalate and amides.

4. A composition according to claim 3, wherein the oxalate acid ester is added to the system in an amount of 1.3 mg/ml.

5. A composition according to claim 2, wherein the fluorescer compound is a member selected from the group consisting of (1-chloro-9, 10-bis (phenylethynyl) anthracene, perylene, (2-chloro-9, 10-bis (p-methoxyphenyl) anthracene, (6,13-bis (p-methylphenyl) ethynyl) naphthacene, rubrene, fluorescein and rhodamine derivatives, coumarins, rubrene sulfonate, pyrene, amino pyrene, Dansyl amino acids, 3-aminofluoranthene, 1-anilinonaphthalene-8-sulfonate, and 2-toluidinylnaphthalene-6-sulfonate.

6. A composition according to claim 5, wherein the fluorescer compound is added to the system in an amount of 1 mg/ml.

7. A composition according to claim 2, also containing a catalyst.

8. A composition according to claim 7, wherein the catalyst is sodium salicylate.

9. A composition according to claim 8, wherein the sodium salicylate is present in the amount of 0.2 mg/ml.

10. A composition according to claim 2, wherein the hydrogen peroxide is present at a concentration of no more than between about $10^{-6}$M and about 1M.

* * * * *